United States Patent [19]

Leigh

[11] 4,306,077
[45] Dec. 15, 1981

[54] PROCESS FOR SEPARATING CIS AND TRANS ISOMERS OF CYCLOPROPANE CARBOXYLIC ACIDS

[75] Inventor: Thomas Leigh, Macclesfield, England

[73] Assignee: Imperial Chemical Industries Limited, London, England

[21] Appl. No.: 86,033

[22] Filed: Oct. 18, 1979

[30] Foreign Application Priority Data

Oct. 27, 1978 [GB] United Kingdom ............... 42265/78

[51] Int. Cl.³ ............................................. C07B 19/00
[52] U.S. Cl. .................................... 562/401; 562/402; 562/506
[58] Field of Search ........................ 562/401, 506, 402

[56] References Cited

U.S. PATENT DOCUMENTS

| | | | |
|---|---|---|---|
| 3,794,680 | 2/1974 | Matsui et al. | 562/506 |
| 3,943,167 | 3/1976 | Suzukamo et al. | 562/506 |
| 3,989,654 | 11/1976 | Honda et al. | 562/506 |

FOREIGN PATENT DOCUMENTS

| | | |
|---|---|---|
| 2547510 | 4/1976 | Fed. Rep. of Germany . |
| 2713538 | 9/1978 | Fed. Rep. of Germany ...... 562/506 |
| 2716898 | 10/1978 | Fed. Rep. of Germany . |
| 1270270 | 4/1972 | United Kingdom . |
| 1426000 | 2/1976 | United Kingdom . |
| 1464327 | 2/1977 | United Kingdom . |

OTHER PUBLICATIONS

Matsui et al., Bull. Agr. Chem., Japan 19, pp. 159–160, (1955).

Primary Examiner—Natalie Trousof
Assistant Examiner—Vera C. Clarke
Attorney, Agent, or Firm—Cushman, Darby & Cushman

[57] ABSTRACT

A process of separating cis and trans isomers of cyclopropane carboxylic acids comprising the step of treating an aqueous solution of a soluble salt of the cis and trans isomers with just sufficient of an acid, for example acetic acid or carbonic acid, to cause precipitation of one isomeric form of the cyclopropane carboxylic acid while substantially all or a major proportion of the other isomeric form remains in solution as the soluble salt. The process may be used, for example, to separate (+)-cis-3-(2,2-dichlorovinyl)-2,2-dimethylcyclopropane carboxylic acid (an intermediate for insecticides) from a mixture of the (+)-cis and (+)-trans acids.

10 Claims, No Drawings

PROCESS FOR SEPARATING CIS AND TRANS ISOMERS OF CYCLOPROPANE CARBOXYLIC ACIDS

This invention relates to a process for obtaining substantially pure cis- and trans-isomers of cyclopropane carboxylic acids from mixtures of the cis- and trans-isomers.

Several esters of cyclopropane carboxylic acids are useful as insecticides, including for example, the 3-phenoxybenzyl and α-cyano-3-phenoxybenzy esters of the following cyclopropane acids:

3-(2-methylpropenyl)-2,2-dimethylcyclopropane carboxylic acid,
3-(2,2-dichlorovinyl)-2,2-dimethylcyclopropane carboxylic acid,
3-(2,2-dibromovinyl)-2,2-dimethylcyclopropane carboxylic acid,
3-(2-chloro-3,3,3-trifluoropropenyl)-2,2-dimethylcyclopropane carboxylic acid,
3-(2-bromo-3,3,3-trifluoropropenyl)-2,2-dimethylcyclopropane carboxylic acid,
3-(2-trifluoromethyl-3,3,3-trifluoropropenyl)-2,2-dimethylcyclopropane carboxylic acid,
and other similar acids.

It will be readily apparent that such acids exist in cis and trans forms as illustrated by the following general formulae:

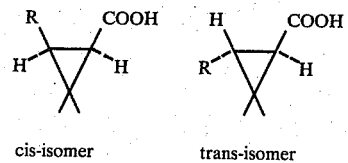

wherein R represents a group other than hydrogen.

The separation of cis- and trans-isomers of cyclopropane propane carboxylic acids has been achieved in the past by, for example, fractional crystallisation of the acids themselves, careful distillation of the lower alkyl esters, or by chemical techniques involving this selective lactonisation of the cis acid or derivatives thereof. These methods are often difficult to perform without substantial losses of the required products in mother liquors, distillation residues, or low yielding chemical reactions.

The present invention concerns a process for separating cis and trans isomers of cyclopropane carboxylic acids which is simple to operate, requires only inexpensive and readily available reagents, and can produce high yields of substantially pure products.

Accordingly the present invention provides a process for separating cis and trans isomers of cyclopropane carboxylic acids of formula:

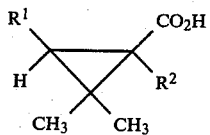

wherein $R^1$ is halo, alkyl, alkenyl, haloalkyl, haloalkenyl, or haloalkynyl, and $R^2$ is hydrogen or cyano, from a mixture of cis and trans isomers, which comprises the step of treating an aqueous solution of a soluble salt of the cis and trans-isomers with just sufficient of an acid to cause precipitation of one isomeric form of the cyclopropane carboxylic acid whilst substantially all or a major proportion of the other isomeric form remains in solution as the soluble salt.

Although any acid having a $pK_a$ which is lower than the $pK_a$ of the isomeric form of the cyclopropane carboxylic acid to be precipitated may be used it is especially preferred to use an acid which has a $pK_a$ which is not lower than the $pK_a$ of the isomeric form of the cyclopropane carboxylic acid which is to remain in solution as the soluble salt since treatment by excess of the acid will not result in unwanted precipitation of that isomeric form. If an acid of lower $pK_a$ is used then the end point of the precipitation of the isomeric form of the cyclopropane carboxylic acid with the highest $pK_a$ should be determined by following the change of pH of the aqueous mixture, or by calculation of the amount of acid to be added when the actual quantities of the cis and transisomers in a particular mixture is known.

The term "acid" as used in relation to the substance which causes the precipitation of cyclopropane carboxylic acid is intended to embrace any substance which when added to the aqueous solution of the soluble salts of the cyclopropane carboxylic acids causes the pH to be lowered sufficiently to cause precipitation of at least one of the isomeric forms of the cyclopropane carboxylic acid. Acids which may be employed include carboxylic acids such as formic acid, acetic acid, propionic acid, and butyric acid, sulphonic acids such as benzene sulphonic acid and toluene sulphonic acid, inorganic mineral acids such as sulphuric acid, hydrochloric acid, nitric acid and phosphoric acid. One particularly useful acid is carbonic acid which is produced by passing in carbon dioxide gas or by adding solid carbon dioxide to the solution of soluble salts.

Suitable soluble salts are preferably ammonium salts and alkali metal salts, and the aqueous solution of soluble salts may be prepared by dissolving the cyclopropane carboxylic acids in an aqueous solution of the hydroxide.

After precipitation the isomeric form of the cyclopropane carboxylic acid may be collected by filtration, and further purified if necessary by crystallisation from an appropriate solvent, or by performing a further cycle of the invention process, although in many cases it will be possible to use the product without any further purification.

In the case of the particular cyclopropane acids evaluated in the Examples herein it is the cis-isomer which is preferentially precipitated, leaving the transisomer in solution. There may be instances of other cyclopropane acids in which the trans-isomer is selectively precipitated.

The process of the invention may also be used to obtain a mixture of the cis and trans isomers containing a higher proportion of one isomeric form from a mixture containing a much lower proportion of that form. Thus for example a mixture containing 80% cis-isomer may be precipitated by carbon dioxide treatment from a mixture containing 40% cis-isomer, and the product used as starting material for a further operation of the invention process to produce substantially pure (i.e. greater than 95%) cis-isomer.

The invention process is illustrated by the following Examples. It is to be understood that the following Examples describe experimental procedures designed to evaluate the scope of the invention process and the conditions used in any particular case are not necessarily those which would lead to the optimum yield or purity of product.

EXAMPLE 1

A mixture of isomeric cyclopropane carboxylic acids (482 g) of the following composition as determined by N.M.R. spectrum measurement, (+)-cis-3-[(Z)-2-chloro-3,3,3-trifluoroprop-1-en-1-yl]-2,2-dimethylcyclopropane carboxylic acid (61%), (+)-trans-3-[(Z)-2-chloro-3,3,3-trifluoroprop-1-en-1-yl]-2,2-dimethylcyclopropane carboxylic acid (34%), (+)-cis-3-[(E)-2-chloro-1,1,1-trifluoroprop-1-en-1-yl]-2,2-dimethylcyclopropane carboxylic acid (2%) and (+)-trans-3-[(E)-2-chloro-3,3,3-trifluoroprop-1-en-1-yl]-2,2-dimethylcyclopropane carboxylic acid (3%) is dissolved in N sodium hydroxide (2 l). Carbon dioxide is passed into the stirred solution until no further precipitation of solid occurs. The mixture is filtered and the residue is washed with water. The solid is dried to obtain almost pure (greater than 95%) (+)-cis-3-[(Z)-2-chloro-3,3,3-trifluoroprop-1-en-1-yl]-2,2-dimethylcyclopropane carboxylic acid (250 g), m.p. 108° C.

EXAMPLE 2

In a similar experiment to that described in Example 1 dilute (2 N) acetic acid (500 cc) was added dropwise over a period of one hour in place of the addition of carbon dioxide. This also resulted in selective precipitation of (+)-cis-3-[(Z)-2-chloro-3,3,3-trifluoroprop-1-en-1-yl]-2,2-dimethylcyclopropane carboxylic acid.

EXAMPLE 3

A mixture of isomeric cyclopropane carboxylic acids (20.9 g) consisting of approximately equal proportions of (+)-cis-3-(2,2-dichlorovinyl)-2,2-dimethylcyclopropane carboxylic acid and (+)-trans-3-(2,2-dichlorovinyl)-2,2-dimethylcyclopropane carboxylic acid was added to a stirred solution of sodium hydroxide (4.0 g) in water (200 ml) and the mixture obtained stirred for 30 minutes, treated with charcoal (3.0 g) and stirred for a further 30 minutes, after which the charcoal and other minor insoluble impurities were removed by filtration. A stream of carbon dioxide gas was passed into the stirred filtrate over a period of 3 hours during which time a white solid was precipitated. The precipitate was collected by filtration, washed with water and dried at the ambient temperature, and shown by proton nuclear magnetic resonance spectroscopy to be a mixture (7.1 g) consisting of 80% by weight of the (+)-cis acid and 20% by weight of the (+)-trans acid, having a melting point of 70°-72° C. The mixture was dissolved in a freshly prepared solution of sodium hydroxide (1.4 g) in water (100 ml), and carbon dioxide gas passed into the solution until precipitation appeared to be complete.

The precipitate was collected by filtration washed with water and air dried. N.m.r. spectroscopy indicated it to be a mixture consisting of 98% of (+)-cis-3-(2,2-dichlorovinyl)-2,2-dimethylcyclopropane carboxylic acid and 2% of the (+)-trans acid, melting at 80°-82° C.

EXAMPLES 4–12

A series of further experiments was carried out using the general procedure of Example 3 but differing in the cis/trans ratio of the starting material [(+)-cis/trans-3-(2,2-dichlorovinyl)-2,2-dimethylcyclopropane carboxylic acid], the dilution factor (expressed as milliliters of water used to prepare the sodium hydroxide solution per gram of starting material), molar scale and time of injecting carbon dioxide into the solution. The experimental details and results obtained are summarised in the following Table.

| EXAMPLE NO | MOLAR SCALE | DILUTION FACTOR | INJECTION TIME (HRS) | CIS/TRANS RATIO % STARTING MATERIAL | CIS/TRANS RATIO % RECOVERED PRECIPITATE | % WT. OF RECOVERED PRECIPITATE |
|---|---|---|---|---|---|---|
| 4 | 0.1 | 19 | 3 | 50/50 | 90/10 | 28 |
| 5 | 0.5 | 9.6 | 3 | 50/50 | 90/10 | 30 |
| 6 | 0.5 | 19 | 3 | 50/50 | 92/8 | 32 |
| 7 | 0.25 | 9.6 | 3 | 40/60 | 80/20 | 33 |
| 8 | 0.5 | 4.8 | 4 | 40/60 | 92/8 | 15 |
| 9 | 0.5 | 19 | 4 | 40/60 | 92/8 | 47 |
| 10 | 0.08 | 10 | 3 | 80/20 | 98/2 | 47 |
| 11 | 0.36 | 10 | 3 | 90/10 | 100/0 | 54 |
| 12 | 0.08 | 10 | 3 | 92/8 | 98/2 | 47 |

I claim:
1. A process for separating cis and trans isomers of cyclopropane carboxylic acids of formula:

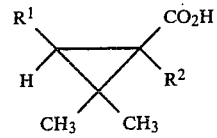

wherein $R^1$ is halo, alkyl, alkenyl, haloalkyl, haloalkenyl or haloalkynyl, and $R^2$ is hydrogen or cyano, from a mixture of cis or trans isomers, which consists essentially of the step of treating an aqueous solution of a soluble salt of the cis and trans isomers with just sufficient of an acid to cause precipitation of one isomeric form of the cyclopropane carboxylic acid whilst substantially all or a major proportion of the other isomeric form remains in solution as the soluble salt, the acid being one having a $pk_a$ lower than the $pk_a$ of the isomeric form of the cyclopropane carboxylic acid to be precipitated.

2. A process as claimed in claim 1 in which the acid has a $pK_a$ which is not lower than the $pK_a$ of the isomeric form of the cyclopropane carboxylic acid which is to remain in solution as the soluble salt.

3. A process as claimed in claim 1 in which the acid is carbonic acid and the process is carried out by treating the aqueous solution of the soluble salt of the cis and trans acids with carbon dioxide.

4. A process as claimed in claim 3 in which a stream of carbon dioxide gas is passed into the aqueous solution.

5. A process as claimed in claim 1 in which the acid is acetic acid.

6. A process as claimed in claim 1 in which the cis-isomer is caused to precipitate.

7. A process as claimed in claim 1 in which (+)-cis-3-[(Z)-2-chloro-3,3,3-trifluoroprop-1-en-1-yl]-2,2-dimethylcyclopropane carboxylic acid is separated from a mixture of itself with (+)-trans-3-[(Z)-2-chloro-3,3,3-trifluoroprop-1-en-1-yl]-2,2-dimethylcyclopropane acid.

8. A process as claimed in claim 1 in which (+)-cis-3-(2,2-dichlorovinyl)-2,2-dimethylcyclopropane carboxylic acid is separated from a mixture of itself and (+)-trans-3-(2,2-dichlorovinyl)-2,2-dimethylcyclopropane carboxylic acid.

9. A process as claimed in claim 1 in which the starting material is a mixture of cis and trans cyclopropane acids containing a higher proportion of one isomeric form obtained by a previous operation of the invention process from a mixture containing a lower proportion of that form.

10. A process as claimed in claim 1 in which the acid is selected from the group of acids consisting of carbonic acid, carboxylic acids, sulphonic acids and inorganic mineral acids.

* * * * *

UNITED STATES PATENT AND TRADEMARK OFFICE
CERTIFICATE OF CORRECTION

PATENT NO. : 4,306,077

DATED : December 15, 1981

INVENTOR(S) : Thomas Leigh

It is certified that error appears in the above-identified patent and that said Letters Patent are hereby corrected as shown below:

On the title page,

[57] ABSTRACT, lines 10 and 12; )
)
Column 3, lines 8, 10, 12, 14, 34, ) each occurrence
43, 49, 50, 63 & 64; )
)
Column 4, lines 3, 5, 10; ) change "(+)" to
)
Column 5, lines 4, 7 & 11; and ) $--(\pm)--$
)
Column 6, line 1; )
)

Signed and Sealed this

Eighth Day of March 1983

|SEAL|

Attest:

GERALD J. MOSSINGHOFF

Attesting Officer     Commissioner of Patents and Trademarks